United States Patent

Taylor et al.

(10) Patent No.: US 6,583,093 B2
(45) Date of Patent: *Jun. 24, 2003

(54) CONDENSATES

(75) Inventors: Spencer Edwin Taylor, Camberley (GB); Michael John Wilson, Pinner (GB)

(73) Assignee: BP Oil International Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/109,848

(22) Filed: Apr. 1, 2002

(65) Prior Publication Data

US 2002/0107153 A1 Aug. 8, 2002

Related U.S. Application Data

(63) Continuation of application No. 09/732,880, filed on Dec. 11, 2000, now Pat. No. 6,399,549.
(60) Provisional application No. 60/189,041, filed on Mar. 14, 2000.

(30) Foreign Application Priority Data

Feb. 7, 2000  (GB) ............................................. 0002779

(51) Int. Cl.$^7$ ........................ C10M 129/14; C10L 1/18
(52) U.S. Cl. ...................... 508/479; 508/502; 508/510; 44/389; 44/403
(58) Field of Search .................. 44/389, 403; 508/479, 508/502, 510

(56) References Cited

U.S. PATENT DOCUMENTS

| | | | | |
|---|---|---|---|---|
| 4,617,336 A | 10/1986 | Pastor et al. | ................ | 524/291 |
| 5,780,403 A | 7/1998 | Moreton | ................ | 508/580 |
| 6,174,844 B1 | 1/2001 | Moreton | ................ | 508/585 |
| 6,200,936 B1 | 3/2001 | Moreton | ................ | 508/479 |
| 6,268,320 B1 | 7/2001 | Crawford | ................ | 508/572 |
| 6,270,537 B1 | 8/2001 | Taylor | ................ | 44/385 |
| 6,399,549 B1 * | 6/2002 | Taylor et al. | ................ | 508/479 |

FOREIGN PATENT DOCUMENTS

WO   99/25677   5/1999

OTHER PUBLICATIONS

Schneider et al, "Synthese und Eigenschaften von Makrocyclen aus Resorcinen . . . ," Chem. Ber. vol. 127, pp. 2455–2469 (1994).

* cited by examiner

Primary Examiner—Ellen M. McAvoy
(74) Attorney, Agent, or Firm—Nixon & Vanderhye

(57) ABSTRACT

A cyclic compound comprising m units of the formula Ia:

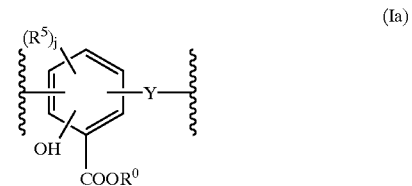

(Ia)

and n units of the formula (Ib):

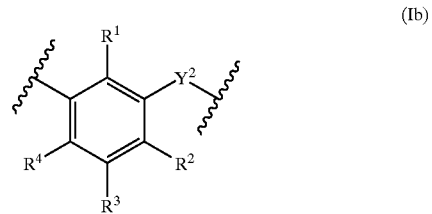

(Ib)

joined together to form a ring, wherein Y and $Y^2$ are divalent bridging groups which may be the same or different in each unit;

$R^0$ is H or ($C_1$–$C_6$) alkyl or is a metal or ammonium cation;

$R^5$ is H or ($C_1$–$C_{60}$) alkyl or OH group;

j is 1 or 2;

$R^3$ is hydrogen, a hydrocarbyl or a hetero-substituted hydrocarbyl group;

each of $R^1$, $R^2$ and $R^4$, which may be the same or different, is hydroxyl, hydrogen, hydrocarbyl or heterosubstituted hydrocarbyl, with the provisos that i) at least one of $R^1$, $R^2$, $R^4$ is hydroxyl, and m+n is 4 to 20, m is 1–8 and n is at least 3, and ii) in formula Ia at least one OH group is in the meta or para position to the $COOR^0$ group and/or at least one $R^5$ group is OH.

19 Claims, No Drawings

CONDENSATES

This application claims the benefit of Provisional Application No. 60/189,041, filed Mar. 14, 2000, the entire content of which is hereby incorporated by reference in this application.

This application is a continuation of application Ser. No. 09/732,880, filed Dec. 11, 2000 the entire content of which is hereby incorporated by reference in this application.

The present invention relates to condensates in particular cyclic calixarene compounds which are cyclic phenolic compounds. The compounds of the invention are particularly suitable as thermal stabilising additives in fuel and for use in lubricating oil compositions for medium or low speed diesel engines, especially four stroke engines. The invention also relates to fuel compositions and to lubricating oil compositions comprising said compounds, e.g. aviation fuel compositions.

In high speed aircraft, both civilian and military, the liquid fuel is combusted to produce power, but also is circulated in the aircraft as a heat exchange fluid to remove the excess heat generated at such speeds e.g. in lubricating oils. The fuel is thus maintained for long periods at high temperatures, which results in discoloration and decomposition to produce soluble coloured products and insoluble products such as gums, sediments and granular material; insoluble products can form deposits that reduce the heat exchange capacity and can block filters potentially causing loss of power. Soluble coloured by-products are unsightly and an indication of some decomposition. The cause of discoloration etc. may be from phenols, naphthenates and sulphur compounds and/or metals which are often present in the fuels.

In some oil fired devices, such as boilers and slow heating cookers, e.g. of the Aga type, kerosine oil fuel is passed down a narrow metal feed pipe to the combustion chamber where it is burnt. Parts of the pipe are sufficiently near the hot chamber for them to be heated to significant temperatures, resulting in the risk of thermal degradation of the fuel in the pipe, especially with slow feed rates and high residence times in the pipe. This degradation can form solid deposits which reduce the flow and ultimately stop it, causing the combustion to stop. To overcome this manufacturers of such devices have for many years recommended to their users that at least once each 6 months such pipe parts are cleaned of solid deposits of coke or other materials.

U.S. Pat. No. 5478367 describes the addition to diesel or jet fuel of a substituted unsaturated polyamine derivative dispersant to reduce particulate emissions on combustion and to reduce fouling i.e. deposition of insoluble deposits. The macrocyclic compounds preferably contain an N=C—N—C=O group and especially have fused rings, such as are made by reaction of a hydrocarbyl (e.g. fatty alkyl) succinic anhydride and a polyalkylene amine.

Canadian Patent Publ. 2067907 describes the addition to distillate jet fuels of hydroxylamines to stabilise them against degradation at elevated temperatures.

U.S. Pat. No. 5468262 describes addition to jet fuels of thermal stability additives which are prepared by reacting a polyamine, aldehyde and phenol to form a condensate which is then reacted with a succinic anhydride containing a polyolefin derived unsaturated group.

The additives are effective at 0.2% by weight.

EP-A-678568 describes addition to jet engine fuels of anti deposition agents which are derivatives of (thio) phosphonic acids.

Accordingly the present invention provides a cyclic compound comprising m units of the formula Ia.

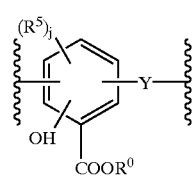

(Ia)

and n units of the formula (Ib)

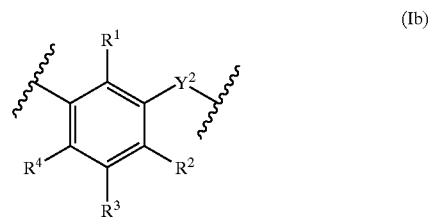

(Ib)

joined together to form a ring,
wherein Y and $Y^2$ are divalent bridging groups which may be the same or different in each unit; $R^0$ is H or $(C_1-C_6)$ alkyl or is a metal or ammonium cation, (so the group $CO_2R^0$ is a carboxylic salt); $R^5$ is H or $(C_1-C_{60})$ alkyl or OH group; and j is 1 or 2; $R^3$ is hydrogen, a hydrocarbyl or a hetero-substituted hydrocarbyl group; each of $R^1$, $R^2$ and $R^4$, which may be the same or different, is hydroxyl, hydrogen, hydrocarbyl or hetero-substituted hydrocarbyl, with the proviso that at least one of $R^1$, $R^2$, $R^4$ is hydroxyl, and m+n is 4 to 20, m is 1–8 and n is at least 3 and preferably either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; and m+n is from 4 to 20, m is from 1 to 8 and n is at least 3, with the proviso that in formula Ia at least one OH group is in the meta or para position to the $COOR^0$ group and/or at least one $R^5$ group is OH. Preferably in a second proviso, at least one of the following features (a) to (e) is met, namely the cyclic compound comprises at least one of (a) at least one formula (Ia) unit in the form of a carboxylate anion especially at least 2 carboxylate anions (b) at least one formula (Ia) unit in the form of an alkaline earth metal or alkali metal carboxylate salt, preferably a potassium or sodium salt, especially a potassium salt (c) at least 2 e.g. 3 or 4 units of formula (Ia) (d) an m+n value of 5–11, preferably 7–9 and especially 8 and (e) the cyclic compound is in the substantial absence of linear species comprising formula (Ia) and (Ib) units and/or or the substantial absence of unreacted formula (Ia) and (Ib) units, (e.g. of formula IIa and IIb hereafter).

Preferably the cyclic compound has at least 2 of (a) (b) (c) (d) and (e) preferably 3, most preferably 4 and especially all 5 in particular (a) and (c), or (b) and (c), and especially (d). In a preferred embodiment the invention provides a cyclic compound wherein m is 2, n is 6, and both the units of formula (Ia) are in the form of a potassium carboxylate salt, and the cyclic compound is in the substantial absence of linear species comprising formula (Ia) and (Ib) units and the substantial absence of unreacted formula (Ia) and (Ib) units.

When more than one $—CO_2R^0$ containing aromatic group unit is present in the ring (i.e. m>1), the phenol units and the $—CO_2R^0$ containing aromatic groups may be distributed randomly, although this does not exclude the possibility that in some rings there may be several $—CO_2R^0$ containing aromatic groups joined together in a row. Thus the m and n units may be joined in block and/or randomly.

If desired, in addition to containing at least one unit of formula Ia, the cyclic compound may also contain at least one unit of formula

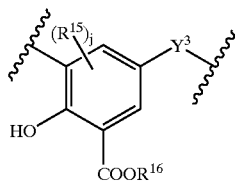

(Id)

where $R^{15}$ is H or $C_{1-60}$ alkyl, and $R^{16}$ and $Y^3$ are as described above for $R^0$ and $Y^2$ respectively. Preferred groups for $R^{15}$, $R^{16}$ and $Y^3$ are as described below for $R^5$, $R^0$ and $Y/Y^2$ (apart from OH for $R^5$). The preferred unit is derived from salicylic acid. The cyclic compound may contain 1–4 units of formula Ia and 1–4 units of formula Id, especially 1 or 2 of formula Ia and 1 or 2 of formula Id, in particular with a total of both of 2 or 3, preferably the cyclic compound consists essentially of units of formula 1a and 1b.

In the formulae Ia/Ib Y, and $Y^2$ may each independently be a hydrocarbyl bridging group or be a hetero-substituted hydrocarbyl group or up to 50% mole of the totality of Y, and $Y^2$ group may be a hetero atom. The hydrocarbyl bridging group is preferably aliphatic and has a chain of 1–4 carbon atoms; preferably the group is of formula $(CR^7R^8)_d$ e.g. $(CHR^8)_d$ where each of $R^7$ and $R^8$, which may be the same or different, represents hydrogen or hydrocarbyl e.g. of 1–20 carbons such as 1–6 carbons or 6–20 carbons, such as methyl or ethyl and d is an integer of 1–4 preferably 2 or especially 1; advantageously the group is of formula $(CHR^8)_d$ where $R^8$ is as defined above preferably methyl or especially hydrogen. Y, and/or $Y^2$ may also represent a hetero-substituted hydrocarbyl group with a hetero atom, e.g. O, S or NH interrupting a chain of carbon atoms e.g. 2–4 carbon atoms, such as in $CH_2OCH_2$, $CH_2SCH_2$ or $CH_2NHCH_2$. Up to 50 mole % of the totality of Y and Y2 groups may be a hetero atom e.g. O or NH or especially 5, e.g. 1–50 mole % especially 8–20 mole % of said groups. Preferably Y and $Y^2$ are hydrocarbyl groups, and the compound of formula I is sulphur free.

In the group of formula Ia, the group Y is usually ortho or para to an OH group and/or is usually meta to the $CO_2R^0$, but can be ortho to said $CO_2R^0$ group, especially when an HO group is meta to the $CO_2R^0$ group. The group Y is usually meta to the free valency in the ring but may be para thereto. In particular, group Y is para to an OH group and meta to a $CO_2R$ group so the group is of formula Ic.

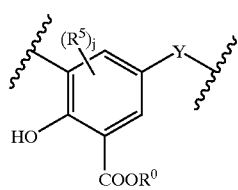

(Ic)

where one $R^5$ is OH and one $R^5$ is hydrogen. In a special subclass the $CO_2R^0$ and OH groups in Ia are meta or para to one another unless there are two OH groups in the ring i.e. one of $R^5$ is OH. When the group Ia contains two OH groups in the ring, they may be ortho or para to one another (as in 2,5, and 3,4, dihydroxy benzoic), but are preferably meta to one another, (as in 2,4, or 3,5 and 2,6 dihydroxy benzoic) especially when none, one or two OH groups is/are ortho to the $CO_2R^0$ group, in particular none or one, and advantageously one. When the group Ia contains two OH groups in the ring, one OH may be in the ortho position and the other be in the ortho, meta or para position relative to the $CO_2R^0$ group. When the group Ia contains only one OH group per ring, that OH group is meta or para but when there is more than one group Ia in the ring i.e. m is at least 2, the second or other group Ia may have the OH group ortho to the $CO_2R^0$ group, so the unit is a salicylic acid derivative.

Preferred units for formula Ia are from a mono hydroxy aromatic carboxylic acid, which is a meta or para hydroxy benzoic acid or a dihydroxycarboxylic acid, which is preferably 2,4, dihydroxy benzoic acid or 3,5,dihydroxy benzoic acid, but may be 2,5, or 2,6, or 3,4,dihydroxy benzoic acid.

When the second proviso in respect of the compounds of formula Ia/Ib applies, the units of formula Ia are preferably of formula Ic, especially when $R^5$ is OH, in particular a resorcylic acid (or salt thereof).

Each of $R^1$, $R^2$ and $R^4$ represents hydroxyl, hydrogen, hydrocarbyl or hetero-substituted hydrocarbyl with the proviso that at least one of $R^1$, $R^2$ and $R^4$ represents hydroxyl. Thus all three may represent hydroxyl as in a phloroglucinol derivative, or two as in a resorcinol derivative (i.e. the compound of formula Ia/Ib contains a resorcinarene group), or one as in a phenol derivative. Preferably either $R^1$ is hydroxyl and $R^2$ and $R^4$ are independently either hydrogen (which is preferred), hydrocarbyl or hetero-substituted hydrocarbyl, or $R^2$ and $R^4$ are hydroxyl and $R^1$ is either hydrogen, hydrocarbyl or hetero-substituted hydrocarbyl.

Regarding $R^1$ to $R^5$ and $R^8$, the term "hydrocarbyl" includes $(C_1-C_{60})$ alkyl such as t-butyl, t-amyl, s-butyl, isopropyl, octyl, nonyl, dodecyl and octadecyl. Alternatively the hydrocarbyl group may be derived from a polyolefin, for example polyethylene, polypropylene, polybutylene or a polyolefin copolymer, for example an ethylene/propylene copolymer, preferably derived from a polyisobutene. Alternatives include isoprene-butadiene, styrene-isoprene or styrene-butadiene block copolymers such as those disclosed in WO 96/40846, or ethylene-propylene and ethylene-butene-1 copolymers having molecular weights from 1500 to 2500 or 7500, as disclosed in U.S. Pat. No. 5,567,344 and U.S. Pat. No. 5,578,237. Mixtures of all the above may also be employed. Any hetero-substituted hydrocarbyl group has the heteroatom, preferably —O— or =NH, interrupting a chain of carbon atoms, such as an alkoxy-alkyl group of 2–20 carbons. Each of $R^1$–$R^5$ may otherwise be as described for $R^3$ below.

The hydrocarbyl group for $R^1$, $R^2$ or $R^4$ usually has 1–14 e.g. 1–6 carbons and is preferably saturated, especially an alkyl group e.g. methyl, ethyl, propyl, butyl or hexyl group. The hetero-substituted hydrocarbyl group has at least one e.g. 1–3 especially 1 hetero atom e.g. O S or NH interrupting a chain of carbon atoms e.g. 2–20, or 2–6 carbons as in an alkoxy alkylene group such as ethoxy ethyl.

$R^3$ is hydrogen, hydrocarbyl or a hetero-substituted hydrocarbyl group. Preferably $R^3$ is hydrocarbyl or a hetero-substituted hydrocarbyl in at least $R^3$ group in the compound of formula I, especially with n such groups in the molecule. The hydrocarbyl group may be alkyl, alkenyl, cycloalkyl, aryl, aralkyl and contains at least 1 especially at least 4 or at least 8 carbon atoms e.g. 4–40 carbons in particular with 8–20 carbons in a chain. Preferred are linear or branched alkyl e.g. of 8–24 or 8–20 carbons, such as decyl, dodecyl, tetradecyl, hexadecyl, octadecyl, lauryl, myristyl, stearyl, palmityl, propylene trimer or tetramer or alkenyl e.g. of 6–24 carbons such as oleyl, or cycloalkyl e.g. of 5–8 carbons such as cyclohexyl, aryl e.g. of 6–24 carbons such as phenyl, tolyl and alkylphenyl with 6–16 carbons in the alkyl e.g. dodecylphenyl and aralkyl e.g. of 7–26 carbons such as benzyl and alkyl substituted benzyl with 6–16 carbons in the alkyl e.g. dodecyl benzyl. $R^3$ may also represent a polymeric hydrocarbyl group e.g. from a polyolefin group, especially from one or more olefins of 2–6 carbons such as ethylene, propylene, butene, isobutene; the polymeric groups may be from polyethylene, polypropylene, polybutene, an ethylene propylene copolymer or polyiso butene (which is preferred). Molecular weights of polymeric $R^3$ groups may be 300–6000 e.g. 500–2000. In the compound of formula I, there may be different $R^3$ groups in the same molecule.

In the compound of formula I, m is from 1 to 8 e.g. 1–4 especially 2 or in particular 1, while n is at least 3 e.g. 3–10, in particular 5–9 especially 6–8. The sum of m+n is 4–20, preferably 5–10 in particular 7–9, e.g. 6 or 8, or a mixture of compounds with m+n having the value of 6 and 8. Preferably m is 1 or 2 and m+n is 5–10 e.g. 8.

In preferred calixarenes Y, or $Y^2$ is $CH_2$; $R^1$ is hydroxyl; $R^2$ and $R^4$ are independently either hydrogen, hydrocarbyl or hetero-substituted hydrocarbyl; $R^3$ is either hydrocarbyl or hetero-substituted hydrocarbyl; $R^0$ is H or is substituted by an alkali metal ion, in particular a potassium ion; $R^5$ is hydrogen or an alkyl group of 6 to 50 carbon atoms, preferably 4 to 40 carbon atoms, more preferably of 6 to 25 carbon atoms; j is 2 or preferably 1; and m+n has a value of at least 5, preferably at least 6, typically at least 8, where m is 1 or 2, preferably 1.

More preferably $R^2$ and $R^4$ are hydrogen; $R^3$ is hydrocarbyl, preferably alkyl of greater than 4, preferably greater than 9 carbon atoms; $R^5$ is hydrogen; and m+n is from 6 to 12 e.g. 8; m is 1 or 2.

In preferred compounds, $R^2$ and $R^4$ are hydrogen, m is 1 or 2, n is 5, 6 or 7, m+n is 6 and/or 8, $R^1$ is hydroxyl, $R^3$ is alkyl of 8–20 carbons e.g. dodecyl or octadecyl, or polyisobutenyl.

The metal in the salt form may be an alkali metal e.g. Li, Na, K, Rb or Cs, or an alkaline earth metal e.g. Mg or Ca, or the salt may be an ammonium or a quaternary ammonium salt e.g. of formula $NR^1R^2R^3R^4$ wherein $R^1$–$R^4$ are as defined above, especially with at least 3 and in particular 4 of them of less than 10 carbons.

For convenience the cyclic compounds may herein be referred to as "carboxy calixarenes".

For a review of calixarenes the reader is referred to 'Monographs in Supramolecular Chemistry' by C David Gutsche, Series Editor-J Fraser Stoddart, published by the Royal Society of Chemistry, 1989. Calixarenes having a substituent hydroxyl group or groups include homocalixarenes, oxacalixarenes, homooxacalixarenes and heterocalixarenes.

Calixarenes of the present invention may be made by reacting together appropriate amounts of the optionally substituted hydroxy benzoic acid e.g. (or carboxylic ester), an optionally substituted phenol, and a carbonyl compound which is preferably an aldehyde e.g. formaldehyde, or acetaldehyde, especially in the presence of a base and optionally a catalyst. The reaction may be performed in the presence of sulphur if the cyclic compound of formula Ia/Ib is to contain combined sulphur.

The calixarenes may be made by a process comprising reacting together, preferably in the presence of a basic catalyst, compounds of the formula (IIb) with one of formula IIa (especially IIc).

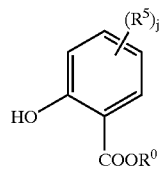
(IIa)

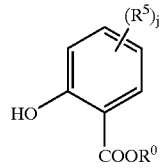
(IIc)

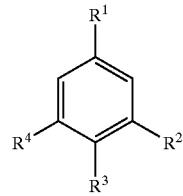
(IIb)

with an aldehyde of the formula $O=CR^7R^8$ e.g. $O=CHR^8$, and optionally sulphur, or with a dihalide $YX_2$ or $Y^2X_2$ where, $R^0$ to $R^5$, $R^7$, $R^8$ and j are as defined previously and X is chlorine, bromine or iodine.

Preferred basic catalysts are alkali metal hydroxides such as sodium hydroxide, potassium hydroxide and lithium hydroxide. The process may also be performed in the substantial absence of a basic catalyst.

A proportion of the product may comprise linear molecules. Linear molecules are also composed of units having formulas (Ia) and (Ib) except that instead of the ends of the molecule being joined to form a ring, each end has a terminal group which is independently one of the following:

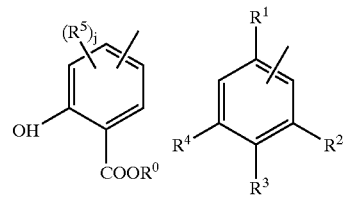
(III)

In the linear molecule the total number of units m+n is from 2 to 20, m is from 1 to 8 and n is at least 1. A further aspect of the invention provides the product (hereinafter called Product A) of reacting compounds of the formulas (IIb) above and IIa (preferably IIc) with an aldehyde of the formula $O=CHR^8$, and optionally sulphur; where $R^0$ to $R^8$ are as defined previously. The reaction product usually comprises at least 20% by weight of a cyclic compound comprising units of formulas (Ia) and (Ib) and no more than 80% of the linear version of said compound. Preferably the cyclic form comprises at least 40%, more preferably at least 60% and most preferably at least 80% by weight of the reaction product. Product A also can include but may exclude products isolated from said reaction product, but preferably include said isolated cyclic products containing the $COOR^0$ group.

The process may be performed with an amount of base which is 0.01–0.2 equivalents per mole of the carboxylic salicylic acid, with the base being effectively in catalytic amount, or with 0.2–10 equivalents per mole of the carboxylic acid.

The process may be performed in a melt or in the presence of water or in a solution or suspension. The water may be added with the base e.g. aqueous sodium or potassium hydroxide solution, and/or a possible solvent for the formaldehyde (e.g. 10–30% formaldehyde solution), the amount of added water being usually 1–20% of the total weight of the reactants e.g. 5–15%. Advantageously the process is performed with the water present initially, and then once reaction has started, then any water present as well as water produced as by product is removed e.g. by evaporation or distillation, whether under reduced pressure, and/or heating at above 110° C.

The process may also be performed in the presence of an inert organic liquid which may be a solvent for at least one of the reactants, e.g. the phenol and/or aromatic carboxylic acid and/or a solvent or non solvent for at least one of the phenolic products, especially a carboxy calixarene such as one of formula Ia/Ib and/or a linear phenolic species. The liquid is usually a hydrocarbon of atmospheric boiling point 100–160° C., such as toluene or a xylene or methylbenzene. The amount of liquid may be 10–90% of the total weight of solvent and reactants, especially 50–90%. Preferably the liquid is immiscible with water and can entrain water in its distillation and/or reflux, e.g. a Dean and Stark apparatus.

The reaction is usually performed at 80–180° C. e.g. 100–150° C. and until substantially no more by product water is produced and separated at the end of the reaction, the solvent if any may be evaporated to leave a crude product, or the reaction product (optionally with solvent) treated or used as such.

The direct product of the process to make the carboxy calixarene may be used as such (i.e. without purification from other phenolic compounds) or may be converted from one salt form to another e.g. via ion exchange or by way of acidification to form the free acids, and then if desired formation of a salt by neutralisation. Preferably the direct product is purified to increase its content of cyclic and/or carboxylic species. The direct product may be distributed between a substantially water immiscible organic solvent e.g. an aliphatic liquid hydrocarbon, such as kerosene or hexane or an aromatic hydrocarbon such as toluene or xylene, and an aqueous medium. The medium may be basic e.g. with an alkali metal hydroxide or especially carbonate or bicarbonate, in which case the aqueous medium can extract the carboxylic species, while the non carboxylic species remains in the organic phase; the phases are then separated and then carboxylic salt recovered from the aqueous phase, or acidified to free carboxylic acid and recovered from an organic phase. The direct product may also be purified, when dissolved in organic solvent, by addition of a compound capable of producing a salt insoluble in the solvent e.g. addition of a barium salt (as such or in organic or aqueous solution) can cause precipitation of an insoluble barium carboxylate salt, which may be separated from the non carboxylic compounds. Acidification of the barium salt enables the free carboxylic acid to be recovered.

The direct product in organic solution is e.g. an aliphatic or aromatic hydrocarbon such as one described above, may be contacted with an anion exchange resin, so that the carboxylic compound(s) are bound to the resin, while the non carboxylic compounds are not. The treated resin may then be separated and treated with alkali metal hydroxide or alkoxide solution to regenerate the resin for reuse and to liberate the alkali metal salt of the carboxylic acid. The process may be batch wise or continuous (with a pair of resins in parallel, one for separation while the other is being regenerated). The resin is preferably a macroreticular one, and usually has quaternary ammonium cationic substituents; an example of such a resin is that sold under the Trade Mark Amberlyst 15.

The direct product may also be purified by shape selective separation by contact of the direct product (in acid or salt form) in organic solution with an inorganic porous solid, whose pores are insufficiently large to allow the carboxy calixarene to enter, but allow the linear products to enter. Preferred maximum diameter for pores are 100A, especially <70 or <50 A and especially above 20A. Examples of such porous solids are silica, alumina and silica/alumina as well as ceramic membranes, e.g. made of alumina or zirconia. The contact may be batch wise, e.g. passage of the direct product onto a bed of the solid and then elution of the cyclic compounds therefrom as the first eluted fraction; such beds may be in columns in parallel, one for separation of the cyclics while the other is being eluted of the other non cyclic materials. Preferably the separation is continuous e.g. in a cross flow made and/or with a tube of ceramic membrane, through the walls of which the non cyclics pass while the cyclics pass down the tube and are concentrated.

The direct product may also be purified by selective extraction e.g. trituration with a suitable organic solvent e.g. as described above especially an aromatic hydrocarbon such as toluene or xylene, and separation of insoluble material from a solution of soluble material, from which soluble material may be recovered by evaporation. Either of the materials may then be used as such in the fuel compositions of the invention or after further purification e.g. as described above.

Preferably to make the compounds of formula Ia/Ib in which at least some, and preferably substantially all, the carboxylic groups are in salt form, the amount of base is at least 0.2 equivalents per mole of the salicylic acid, in particular 0.2–10, such as 0.9–5 especially 2–5 or about 1. The base chosen is usually the one which provides the cations required in the product, e.g. sodium or potassium hydroxide or carbonate to provide sodium or potassium carboxy calixarene salt. If desired the base for the reaction may be different, and then the reaction product salt may be converted into the desired salt e.g. via ion exchange. Thus an alkali metal base can be used in the reaction and the salt converted to for example quaternary ammonium or calcium, salt form. In addition instead of adding the hydroxy aromatic carboxylic acid as free acid into the reaction process a preformed salt thereof may be used, e.g. sodium or potassium resorcinylate, in the form for example of a solid or in aqueous solution.

Preferably to make the compounds with at least 2 carboxylic acid groups per ring, whether those groups are in acid or salt form or both, the process preferably involves reaction of the hydroxy aromatic carboxylic acid e.g. resorcinylic acid and the phenol in a molar percentage of at least 20% carboxylic acid e.g. resorcinylic acid units based on the total of carboxylic e.g. resorcinylic acid and phenol e.g. 20–90%, such as 20–40%. Advantageously the amount of base present is 0.2–8 equivalents, based on the equivalents of carboxyl groups in the carboxylic acid e.g. resorcinylic acid e.g. 2–5 equivalents.

Preferably to make the carboxy calixarenes with a ring containing 5–11 aromatic rings (derived from the phenol and the carboxylic acid), especially with 7–9 such aromatic rings, and 1–3, in particular 2 or 3 carboxyl containing phenolic rings e.g. resorcinylic rings, the process usually involves the presence of a base with a cation of appropriate size, the larger the cation the larger the ring. Thus while a spread of carboxy calixarenes ring sizes is obtained, the average is usually lower for Li e.g. 5–7, than Na e.g. 6–8, than K 7–9 and Cs 9–11.

The fuel or lubricating composition e.g. jet fuel composition may also contain a non ring i.e. linear form of the compound of formula Ia/Ib i.e. with structural units as shown in the Formulae Ia/Ib but terminated usually by the phenol and/or hydroxy aromatic carboxylic acid e.g. resorcinylic acid units.

The present invention also provides the use of at least one of these carboxylic calixarenes of the invention i.e. of formula Ia/Ib or Product A to reduce the discoloration on heating of fuel compositions e.g. jet fuel and fuel compositions comprising kerosine.

The preferred additive is dodecyl-resorcinylic calix[8] arene, which is a resorcinylcalix[8]arene comprising 7 dodecyl substituted phenolic units and one resorcinylic acid unit joined by methylene bridges. Another preferred compound is the corresponding calixarene with 2 resorcinylic groups and 6 dodecylphenol units, preferably at least partially as an alkali metal salt e.g. potassium salt and especially in the form of the dipotassiumi salt.

The additive may be present in the composition in amount of at least 1, e.g. at least 5 ppm, such as 1–1000, 5–1000 e.g. 5–500 especially 5–200 or 10–100 ppm based on the weight of the composition e.g. the jet fuel composition. The additive may be mixed with the jet or other fuel composition in the form of a concentrate in solution, e.g. in an aliphatic aromatic hydrocarbon in 20–80% w/w solution, or it may be added as such to give a solution in the fuel. More than one of the carboxy calixarenes may be present e.g. 2–4, especially differing only in the values of at least one of m and n, especially n.

The composition can comprise jet fuel. The composition can comprise kerosine, in particular in jet fuel. The main component of the jet fuel itself is usually a middle boiling distillate boiling point in the range 150–250° C. at atmospheric pressure and the fuel is usually kerosine which may be mixed with gasoline and optionally light petroleum distillate as in mixtures of gasoline and kerosene. The jet fuel may comprise mixtures of gasoline and light petroleum distillate, e.g. in weight amounts of 20–80:80–20 such as 50–75:50–25 which weight amounts may also be used for mixtures of gasoline and kerosene. The jet fuels for military use are designated JP4 to 8 e.g. JP4 as 65% gasoline/35% light petroleum distillate (according to US Mil. Spec. (MIL 5624G)), JP5, similar to JP4 but of higher flash point, JP7, a high flash point special kerosene for advanced supersonic aircraft and JP8, a kerosene similar to Jet Al (according to MJL 83 133C). Jet fuel for civilian use is usually a kerosene type fuel and designated Jet A or Jet Al. The jet fuel may have a boiling point of 66–343° C. or 66–316° C. (150–650° F. e.g. 150–600° F.), initial boiling point of 149–221° C., e.g. 204° C. (300–430° F., e.g. 400° F.), a 50% boiling point of 221–316° C. (430–600° F.) and a 90% boiling point of 260–343° C. (500–650° F.) and API Gravity of 30–40. Jet fuel for turbojet use may boil at 93–260° C. (200–500° F.) (ASTM D1655–59T). Further details on aviation fuels may be obtained from "Handbook of Aviation Fuel Properties", Coordinating Research Council Inc., CRC Report No. 530 (Society of Automotive Engineers Inc., Warrendale, Pa., USA, 1983) and on US military 25 fuels, from "Military Specification for Aviation Turbine Fuels", MIL-T-5624P.

The jet fuel may be the straight run kerosene optionally with added gasoline, but preferably has been purified to reduce its content of components contributing to or encouraging formation of coloured products and/or precipitates. Among such components are aromatics and olefins and mercaptans. Thus the fuels may be purified to reduce their mercaptan content e.g. Merox fuels and copper sweetened fuels or to reduce their sulphur content e.g. hydrofined fuels or Merifined fuels. Merox fuels are made by oxidation of the mercaptans and have a low mercaptan S content (e.g. less than 0.005% wt S) such as 0.0001–0.005% but a higher disulphide S content (e.g. at most 0.4% or at most 0.3% wt S such as 0.05–0.25 e.g. 0.1–2%); their aromatic (e.g. phenolics) and olefins content are hardly changed. Hydrofined jet fuels are ones in which the original fuel has been hydrogenated to remove at least some of sulphur compounds e.g. thiols and under severe conditions to saturate the aromatics and olefins; hydrofined jet fuels have very low sulphur contents (e.g. less than 0.01% S by weight). Merifined fuels are fuels that have been extracted with an organic extractant to reduce or remove their contents of sulphur compounds and/or phenols. The jet fuel may also contain metals, either following contact with metal pipes or carried over from the crude oil; examples of such metals are copper, nickel, iron and chromium usually in amounts of less than 1 ppm e.g. each in 10–150 ppb amounts. Merox and hydrofined fuels are preferred and may be used in JP 4–8 jet fuels.

The fuel comprising kerosine may also be a fuel for combustion especially for non motive purposes, e.g. power generation, steam generation, and heating, especially for use 15 in buildings and for cooking, e.g. as described above. The fuel is particularly suitable for the devices e.g. boilers and slow cookers as described above in which there is localised preheating of the fuel before it is combusted. Such fuels are known as burning kerosine and may have the same physical properties as the kerosine based jet fuels described above, e.g. straight run kerosine, or kerosine modified to reduce its content of at least one of aromatics, olefins and sulphur compounds, as described above. The fuel may also contain metals as described above.

The fuel compositions of the invention contains the cyclic compound of formula Ia/Ib and may also contain at least one conventional additive e.g. for jet fuels or burning fuels such as an antioxidant, corrosion inhibitor, dispersant/detergent, (in particular in the case of hydroxy carboxylic acids (see below)), especially in amounts each of 1–1000 ppm, e.g. 20–200 ppm. The carboxy calixarenes i.e. additives of formula Ia/Ib may be present in the composition especially with a dispersant; the dispersant is in particular one for solids known for use in fuels e.g. automotive burning or aviation fuels. Such dispersants usually have a polymeric carbon backbone with pendant groups containing nitrogen, which may be primary, secondary or tertiary, in cyclic or acyclic systems, and especially in amine, amide or imide groupings, in particular cyclic imide groups. The dispersants may also contain 1–5 polymer chains which are bridged by the nitrogen containing groups. Examples of such dispersants are the reaction products of polyisobutene succinic anhydride (PIBSA) and polyamines. Such dispersants are known compounds for dispersing particles of in non aqueous systems e.g. hydrocarbon systems. The weight ratio of carboxy calixarene to dispersant may be 99:1 to 10:90, especially 30:70 to 70:30. The additives and the fuel composition are preferably substantially ashless. Burning kerosine is usually substantially free of the above additives apart from that of formula Ia/Ib.

The fuel compositions of the invention containing the compounds of formula Ia/Ib, have an improved thermal stability as shown by a reduced tendency to discolour and/or produce solids on heating compared to the fuel alone (in the isothermal corrosion and oxidation test (ICOT based on ASTM D487 1)). In some cases the combination of the compounds of formula Ia/Ib or Product A and certain other hydroxy carboxylic acid derivatives imparts to some fuels further improved stability still, better than either additive alone. This synergistic behaviour is found with combinations of the compound of formula Ia/Ib and the hydroxycarboxylic acid in Merox fuels.

Thus in a preferred embodiment the invention also provides a blend comprising at least one compound of formula Ia/Ib or Product A and at least one hydroxy carboxylic acid (different from said compound) with at least one chain of at least 8 carbon atoms. The invention also provides a fuel composition comprising said blend and a fuel comprising kerosine and/or a jet fuel which is a Merox fuel, especially one which has a mean deposit forming tendency in the ICOT test according to ASTM D4871 of 80–120mg deposit per liter of fuel, in particular 80–105mg/l.

In the blend of this invention the weight ratio of the compound (c) of formula Ia/Ib to hydroxycarboxylic acid is usually 10–90:90–1, in particular 30–85:70–15 and especially 35–65:65–35. The amount of the blend in the fuel is usually 10–1000 ppm e.g. 30–200 ppm.

The hydroxycarboxylic acid contains in total at least 1 hydroxyl group e.g. 1–4 such as 2 or 3 but preferably 1 hydroxyl group. It usually contains a hydroxyl group on a carbon atom alpha, beta or gamma to the carbon atom to which the carboxylic acid group is bonded and may optionally have 1 or more hydroxyl groups elsewhere in the molecule: preferably the only hydroxyl group in the molecule is in the alpha, beta or gamma especially the beta position. The hydroxy acid may be of formula,

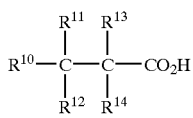

wherein one of $R^{11}$ and $R^{13}$ represents hydrocarbyl and the other hydrogen or an organic group, each of $R^{10}$, $R^{12}$ and $R^{14}$, which may be the same or different, represents hydrogen or an organic group, bonded via carbon or a heteroatom, which is O, N or S, with the proviso that at least one, and preferably only one of $R^{10}$–$R^{14}$ represents an organic group containing a carbon chain of at least 8 carbon atoms. Examples of the organic groups, bonded via carbon are alkyl, cycloalkyl, alkenyl, aralkyl or aryl, e.g. as described for $R^3$ above, especially an alkyl group of 8–3 000 carbons, in particular 8–24 carbons especially dodecyl, octadecyl, and 50–3000 carbons e.g. polyolefinyl such as from polyisobutene. Examples of the organic group bonded via nitrogen are amino groups with long chain hydrocarbyl group e.g. 8–24 carbons, or amido or imido groups from long chain carboxylic acids with 8–3000 carbons, e.g. 8–24 carbons such as fatty acids e.g. stearic and palmitic acids, or 50–3000 carbons e.g. polyolefinyl such as from a carboxylic derivative from polyisobutene such as PIBSA. In particular $R^{11}$ preferably represents hydroxyl/or hydrogen, $R^{10}$ represents hydrogen or a long chain hydrocarbyl group of at least 8 carbons, especially 8–24 or 50–3000 carbons, $R^{12}$ represents hydrogen or alkyl of 1–6 carbons e.g. methyl or ethyl, $R^{13}$ represents hydroxyl or hydrogen and $R^{14}$ represents hydrogen or a amino, amido or imido group with a long chain aliphatic group or long chain mono or di acyl group, in particular a long chain succiic imide e.g. PIBSA. Especially $R^{10}$ or $R^{14}$ contains a long chain aliphatic group but not both. Preferred examples of the hydroxy carboxylic acid are N(long chain acyl) derivatives of beta hydroxy amino acids e.g. serine and threonine and long chain hydrocarbyl alpha hydroxy acids e.g. 1-hydroxy dodecanoic, 1-hydroxypalmitic and 1-hydroxystearic acids, 1-hydroxyl polyiso butenyl-1-carboxylic acid (from PIB aldehyde).

The invention also provides a fuel composition comprising liquid hydrocarbons, at least a majority of which boil at atmospheric pressure at 251–350° C. (according to ASTM D86). The hydrocarbon fuel may be diesel oil (e.g. as defined in European Standard EN590:1993, the disclosure of which is herein incorporated by reference), but is preferably gas oil (e.g. as defined in its European Standard the dislcosure of which is herein incorporated by reference), especially with a boiling range of 251–410° C. The gas oil is a hydrocarbon fraction boiling between kerosine and light lubricating oil. The gas oil may be straight run gas oil, from direct distillation of crude oil under atmospheric pressure, cracked gas oil, which has the above boiling range and is made by distillation of the product of cracking high boiling or other oils either thermally or catalytically, or vacuum gas oil, with the above boiling range made by vacuum distillation of a residue, e.g. from a crude oil distillation or cracked oil distillation, or visbroken gas oil, made by treating one of the above gas oils to reduce its viscosity. The liquid hydrocarbon in the fuel composition may also be a product of hydrotreating or hydrofining a gas oil as described above; more information on these is provided below.

The fuel composition can thus contain at least a majority of a gas oil e.g. 51–100% (of the liquid hydrocarbons) e.g. at least 70% such as 70–90%, with usually up to 30% by weight (of total liquid hydrocarbons) of liquid hydrocarbons boiling above or below the gas oil, e.g. kerosine bp 150–250° C. and heavy gas oils of Final Boiling Point 350–410° C. Blends comprising a majority of gas oil with a minority of kerosene, or a majority of gas oil with a minority in total of kerosine and the heavy gas oil are preferred. The fuel composition may contain one or more of the types of gas oil discussed above, preferably with straight run gas oil and at least one other gas oil, especially with at least 50% or at least 70% of the straight run gas oil and up to 30% in total of one or more other gas oils e.g. cracked gas oil.

The fuel of the invention may comprise diesel fuel itself e.g. for use in diesel engines for motive use such as automobiles, trucks and buses, rather than the cruder gas oil, which contains diesel and a wide range of liquid hydrocarbons of boiling point above and below diesel. The gas oil is preferred for non motive uses. The fuel may also comprise biofuel from vegetable and/or animal sources, such as rapeseed oil esters e.g. the methyl ester, especially in weight ratios to liquid hydrocarbons of bp 251–350° C. of 5–30:95–70.

The liquid hydrocarbons in the fuel of the invention may have at least one of and preferably all of the following distillation properties 220–250° C. an initial bp (IBP) of 140–220° C., a 10% distillation point of 190–250° C., 50% distillation point of 220–250° C., 90% distillation point of 280–380° C. (e.g. 300–350° C.) 95% distillation point of 320–380° C. (e.g. 340–360° C.) and a Final Boiling Point of 290–385° C. (such as 330–360° C.).

The hydrocarbons may have Conradson Carbon contents (by weight) of 0.01–1 e.g. 0.01–0.1 or 0.1–1. They may have aniline points of 40–80° C. e.g. 60–75° C. (as in gas oils) or 10–40 e.g. 15–30 (as in diesel oil). They may have a Specific Gravity of 0.80–0.90, e.g. 0.82–0.88 or 0.82–0.86, and a minimum Flash Point of at least 38° C. (Closed, Abel.) or at least 55° C. such as 75–95° C. (Closed Pensky Martens). The cetane Number may be at least 40, 45, 49 or 51 such as 40–55, e.g. 45–48 or 49–54, but especially 40–49 or 45–49 as in gas oil. The sulphur chemical analysis may be less than 0.5% sulphur compounds (expressed as elemental S) such as 0.0001–0.5%, preferably less than 0.2% or 0.05% or 0.01%S, such as 0.05–0.2%S. The aromatic contents of the liquid hydrocarbons is usually less than 40% total aromatics e.g. 20–40% but especially less than 20% such as 5–15% total aromatics.

The liquid hydrocarbons e.g. gas oil or diesel preferably have been purified to reduce their content of components contributing to or encouraging formation of coloured products and/or precipitates or sulphur oxides on combustion. Among such components are aromatics and olefins and sulphur compounds. Thus the fuels may be purified to reduce their sulphur content e.g. in a corresponding manner to that described above for jet fuel e.g. hydrofined fuels or Merifined fuels. The fuel of the invention may also contain metals, either following contact with metal pipes or carried over from the crude oil; examples of such metals are copper, nickel, iron and chromium usually in amounts of less than 1 ppm e.g. each in 10–150 ppb amounts. Hydrofined fuels are preferred.

The fuel compositions of the invention include the cyclic compound of formula Ia/Ib or Product A and may also contain at least one conventional additive for automotive, heating or burner fuels e.g. an antioxidant, corrosion inhibitor, stabilisers, pour depressant, demulsifiers, antifoams, cetane improvers, lubricity additives, anti-static additives, dehazers, lubricity additives package compatibilisers and dispersant/detergent, (in particular in the case of hydroxy carboxylic acids (see below)), especially in amounts each of 1–1000 ppm, e.g. 20–200 ppm. The carboxy calixarene additives of formula I may be present in the composition especially with a dispersant; the dispersant is in particular one for solids known for use in fuels e.g. heating or burner fuels. Such dispersants usually have a polymeric carbon backbone with pendant groups containing nitrogen, which may be primary, secondary or tertiary, in cyclic or acyclic systems, and especially in amine, amide or imide groupings, in particular cyclic imide groups. The dispersants may also contain 1–5 polymer chains which are bridged by the nitrogen containing groups. Examples of such dispersants are the reaction products of polyisobutene succinic anhydride (PIBSA) and polyamines. Such dispersants are known compounds for dispersing particles of in non aqueous systems e.g. hydrocarbon systems. The weight ratio of carboxy calixarene to dispersant may be 99:1 to 10:90, especially 30:70 to 70:30. The additives and the fuel composition are preferably substantially ashless.

The fuel compositions of the invention containing the compounds of formula Ia/Ib or Product A, have an improved thermal stability as shown by a reduced tendency to discolour and/or produce solids on heating compared to the fuel alone. In some cases the combination of the compounds of formula Ia/Ib or Product A and certain other hydroxy carboxylic acid derivatives imparts to some fuels further improved stability still, better than either additive alone in particular with Merox fuels.

Thus the fuel composition may also include at least one hydroxy carboxylic acid 20 (different from said compound) with at least one chain of at least 8 carbon atoms. Examples of these other hydroxy carboxylic acids are given above in relation to the use in jet fuel or kerosene.

The fuels of the invention may be used in combustion apparatus for motive use or in particular for non motive use in which the fuel is subjected to heating to a temperature e.g. of 100–400° C. such as 200–300° C. before combustion e.g. by proximity to the combustion chamber or otherwise (which may be at 500–700° C.). The feed pipes to the combustion chamber are usually made of metal e.g. copper or steel such as stainless steel, which may become corroded resulting in metal leaching into the oil encouraging degradation. The oil may be emitted into the chamber via a nozzle which becomes hot. The combustion may be in a vaporising burner in which metal in the burner chamber is heated by the flame and in turn vaporises the fuel; examples of such burners are vaporising and pot burners. The combustion is preferably in an atomising burner in which the fuel is atomised either directly, as in pressure jet burners (of low, medium or high pressure) (including simple and wide range burners) and blast burners, or indirectly as in rotary cup burners in which a sheet of fuel is made first and then atomised by contact with air. The atomising burners usually have a hot nozzle on and in which degradation deposits can form. The combustion apparatus may be used to produce heat directly as in industrial furnaces, e.g. for metals or ceramics, or industrial or domestic central heating and cooking as in slow cookers (e.g. of the Aga type) or for raising steam, e.g. process steam. Primarily the apparatus is used for raising power as in gas turbines for electrical power generation.

The invention also provides lubricating oil compositions suitable for 'medium- or low-speed diesel engines, typically the four-stroke trunk-piston engine comprising said cyclic compound. Details of suitable lubricating oils and their other additives in addition to the cyclic compound are described in WO 9925677, the disclosure of which is hereby incorporated by reference, and the corresponding salts e.g. overbased calcium salts of the cyclic compound by analogy to those in WO 9925677 may be used in the lubricating oils of the invention.

In addition to the improved thermal stabilising effect imparted by the compounds of formula Ia/Ib to the fuels, the compounds have now been shown to have improved water tolerance properties. Fuels often pick up water during transport or as a contaminant, in particular in storage or processing. The presence of the water in the fuel is a problem if the fuel contains additives having surface active properties, because the latter stabilise emulsions of water and fuel, especially those made in high speed pumps e.g. in fuel transport lines. The stabilised emulsions increase the viscosity of the fuel. In addition when the fuel is gasoline, e.g. especially aviation fuel, such as jet fuel or aviation gasoline, the presence of water in the fuel is very disadvantageous, because in bulk form, the power developed on combustion is uneven and in bulk and droplet form it contributes to icing of the fuel on cooling, resulting in blocking of fuel jets causing loss of power, either temporarily or permanently. Thus many fuels especially aviation fuels are passed through coalescers en route from refinery to user to convert dispersed droplets of water to separable size droplets, which are then removed. The presence of any additives in the fuel with surface active properties causes the coalescers to fail and therefore the water not to be removed.

The compounds of formula Ia/Ib or Product A have a reduced tendency to stabilise emulsions of water, fuels and compound, compared to some known thermal stabilisers for aviation fuel, or detergents for formulated diesel or formulated gas oil (or for diesel base or gas base fuel (i.e. the hydrocarbon oil in the middle distillate boiling range)). By use of the compounds of formula Ib/Ib or Product A, the separation of water from the fuel is rendered more easy than with the other additives with less production of emulsions and intermediate phases between oil and water (according to the Institute of Petroleum IP 279/97 test), or faster breakage of dispersions (e.g. according to the ASTM D-1094 test). Thus the compounds are phase distinguishers helping to maintain a clear distinction between the water and oil phases, in contrast to the other additives which tend to reduce the distinction between or clarity of or sharpness of the interface between the oil and water.

The present invention provides a method of purifying a mixture of an oil Product which is a liquid fuel or lubricating oil composition, with at least one additive and water, at least part of the water being in the form of a dispersion of water in said Product, which method comprises providing said mixture in which said additive is an Additive (which herein means a compound of formula Ia/Ib or Product A hereinbefore), coalescing at least part of said water in said dispersion into separable droplets of water and separating said droplet water from an oil phase comprising the oil Product and Additive of reduced non-dissolved water content, especially one substantially free of non-dissolved water, e.g. water droplets or dispersion droplets. In the separation there are preferably produced water droplets and an oil phase, and no significant amount of interface material of oil and water. The method is preferably applicable when the oil Product is a hydrocarbon fuel, especially aviation fuel which may contain or may be substantially free of non-hydrocarbon performance additives (apart from the Additive) especially additives officially approved for aviation use.

The separation of water from fuels is performed at least once during the transport of the fuel from where it is made, in one part of a refinery, to the energy user, e.g. an engine of a means of transport on land, on or under sea, or in air, or an engine of a power ore heat generator e.g. an electricity generator or heating boiler. For diesel and gasoline, water may be separated once during the transport of fuel, e.g. in a refinery or blend terminal after it leaves storage, but because of the greater importance of use of substantially water free aviation fuels, water may be separated from aviation fuels more than once during the fuel transport e.g. 2–6 times, such as after any storage e.g. in a refinery, blend terminal or airport storage tank, especially just before the fuel is passed at the airport to refuel an aeroplane or helicopter or hovercraft.

The mixtures of water, fuel and Additive especially compound of formula Ia/Ib, e.g. dispersions, are usually substantially free of anti-icing additives, especially for aviation fuel e.g. jet fuel, as are the fuels ready for combustion (i.e. as passed to the energy user) which comprises the purified fuel composition comprising fuel and said compound.

The presence of water is also a problem in lubricants, both for land based vehicles, such as cars, trucks, buses and trains, and sea based transport e.g. ships, where marine lubricants need to function in the presence of sea water. The invention also provides the use of the compound of Additive especially formula Ia/Ib to restrict the formation of emulsions of water in a lubricant oil.

The oil Product to be purified in the method of the invention may be a blend of a first oil Product, especially a hydrocarbon fuel comprising said Additive, and a second oil Product, especially a hydrocarbon Fuel, which may be the same or different from the first oil Product and may contain, but preferably does not contain said Additive, each of the first and second oil Products being contaminated with water or susceptible of contamination with water.

Thus the present invention also provides a method of purifying an oil Product in which a first liquid oil Product comprising an additive is blended with a second liquid oil Product, at least one of said oil Products, and especially both, being contaminated with water or susceptible to subsequent contamination with water, water is mixed with one or both said oil Products if not already present therein, to produce a 2 phase mixture of said first and second oil Products, additive and water, at least some of the water being in a water in oil dispersion form, wherein said 2 phase mixture in which said additive is an Additive as herein before defined, is coalesced to produce water droplets, and the water is separated from an oil Product comprising said Additive of reduced water content. Preferably said oil Product is substantially free of undissolved water. Preferably the first oil Product is substantially free of non-dissolved water when it is blended with the second oil Product, which may or may not at that time contain undissolved water.

Thus the present invention also provides a blend of at least 2 liquid oil Products e.g. fuels, a first liquid oil Product comprising a first fuel or lubricant base, said Additive and dissolved water, and optionally undissolved water, and a second oil Product, e.g. fuel comprising a second fuel or lubricant base, which may be the same or different from the first base, and undissolved water. The fuel or lubricant bases may contain or may be substantially free of performance additives.

Instead of or as well as the first oil Product, e.g. fuel, comprising Additive being blended with said second oil Product, e.g. fuel, the invention is also beneficial when the second oil Product is passed separately through a line down which the first oil Product has passed, because in many cases the first passage of first oil Product leaves trace of said oil Product and Additive in this line, and/or the walls of the line have adherent or adsorbed Additive, removed from said first oil Product. By this means the second oil Product becomes contaminated with said Additive which in the case of other additives have adversely affected its water tolerance properties; this effect is greatly reduced with the Additives compared to the known thermal stabilisers.

Thus the present invention also provides a method of transporting at least 2 oil Products, e.g. fuels, separately along the same line, each oil Product e.g. fuel being contaminated with water or susceptible to contamination with water, wherein the earlier oil Product passing along the line comprises said Additive, and after passage down said line each oil Product containing water at least partly in dispersion form, is coalesced to produce droplets of water which are separated to leave an oil Product of reduced water content, especially substantially free of non-dissolved water, and preferably with substantially no interface e.g. less than 10% (based on the total value of separated water and interface).

In all the above methods of the invention, a benefit of the invention is that with some other thermally stabilising additives, there are substantial interface problems of the stage of separation of the drops e.g. with an amount of interface of at least 20% (of the value of separated water and interface).

The Additives have the effect of thermally stabilising the oil Products e.g. lubricant such as automative or marine lubricant and fuels e.g. aviation fuel, diesel, gas oil or gasoline, and also of not causing significant interfacial problems when water is separated from mixtures of the oil Product. This latter property is very important commercially for reasons as explained above.

Thus the present invention also provides the use (a) of the Additive to stabilise thermally a liquid oil Product e.g. fuel, especially a jet fuel, while at the same time rendering the stabilised oil Product substantially water immiscible or rendering it substantially non-emulsifiable to water. The use is thus of a combined heat stabiliser and phase separator.

The invention also provides the use (b) of the Additive to stabilise thermally a liquid oil Product, e.g. fuel, especially a jet fuel, without substantially affecting its interfacial tension (e.g. by less than 20% of the value of the oil Product e.g. fuel without the Additive). This use is thus of a combined heat stabiliser and interfacial tension maintainer. This technical effect is in contrast to other known thermal stabilisers, e.g. for jet fuel that have a significant surface active effect and severely reduce the interfacial tension of the fuel (e.g. by more than 30% of the value of fuel without the stabiliser).

The invention also provides the use (c) of the Additive to stabilise thermally a liquid oil Product e.g. fuel, while enabling it also to pass the single element test as defined as in the current edition of API 1581 (Specification and Clarification procedures for Aviation Jet Fuel Filter/Separators).

The Additive also can have a dispersant effect in diesel and/or gasoline, instead of or as well as a thermal stabiliser effect, so the above uses a-c can also be expressed in a similar manner with the two technical effects being the dispersant effect (rather than the thermal stabilising effect) and the non-emulsion stabilising effect e.g. phase separator or interfacial tension maintainer effect.

In addition known thermal stabilisers, e.g. for jet fuel, also adversely affect the active surfaces of coalescers, in which the fuel with dispersed water contacts the active surface effecting coalescing of the dispersed water droplets causing then to grow from a size of less than 1 micron to produce droplets of size at least 1 mm. The active surface of a successful coalescer is sufficiently hydrophilic to have the above effect, but in the presence of the known stabiliser the surface becomes more hydrophobic and tends to lose its coalescence power. Eventually the coalescer cannot fulful its function of coalescing water in the fuel and has to be replaced. The Additives have a much reduced effect on the active surface of the coalescer compared to the known stabiliser, thereby increasing the lifetime of the coalescer.

The present invention therefore also provides a method of increasing the lifetime of a coalescer, which is used to coalesce water present in a water dispersion in an oil Product, which comprises having in the oil Product an Additive. The dispersion of water oil Product and Additive is converted into droplets of water or a separate water phase, and an oil Product phase containing the Additive of reduced non-dissolved water content, and preferably substantially no interface of water and oil Product.

The coalescer usually comprises a fibre bed, often of different fibre diameters, pore size or density. The overall bed may be a random mixture of the above fibres, but preferably is in graded layers, to coalesce dispersions of wide range of water droplet sizes. The fibres usually have an affinity for water but are not completely hydrophilic; they may be polymeric with polar groups e.g. CONH, —COO—, but not alcoholic OH, as in cellulose, or cellulose ethers or esters; these fibres are of non-cellulosic polar polymers. Alternatively the fibres can be inorganic e.g. glass fibre especially glass treated with polar molecules such as glass treated with an organoxy-aminoalkyl silane or glass fibres bonded with phenolic resins e.g. phenol formaldehyde resins; these are hydrophobised inorganic fibres.

Coalescers and their structure and apparatus describing them are described in R. L. Brown and T. H. Wines, Hydrocarbon Processing December 1993 pp95–100 the disclosure of which is herein incorporated by reference.

The invention is illustrated in the following Examples.

EXAMPLES

Preparation of alkyl beta resorcyclic calixarenes.

EXAMPLE 1

A reaction was performed between tertbutyl phenol (6 equivs) 2,4-dihydroxy benzoic acid (1.71 g, 2 equivs.) and paraformaldehyde (2.66 g) in the presence of pellets of potassium hydroxide (1.0 g, slightly more than 2 equivs.). The reactants were placed in a two necked 100 ml flask fitted with a condenser to collect distillate, dry mixed there and then warmed in a heating mantle. The uniform liquid mixture was then heated in a distillation apparatus to drive off the by product water give off during the condensation reaction. Completion of the condensation reaction was signalled by a reduction in rate of emission of vapour and a general viscosifying and darkening of the liquid reaction product. At this stage, toluene (ca. 30 ml) was added to the reaction mixture and refluxed for approx. 1 hr to provide a suspension. The suspension was evaporated to leave a product which gave a positive result in a Rhodamine B test, commensurate with the presence of a tert butyl beta resorcylic calixarene. The suspension may also be filtered to product a first solid product and a solution which may be evaporated to leave a second solid product.

EXAMPLE 2

The process of Ex. 1 was used with reaction of 5.0 g of paranonylphenol and 1.31 g of 2,4-dihydroxybenzoic acid and 1.45 g of paraformaldehyde and 0.63 g potassium hydroxide. Reaction started after 3 mins and the reaction contents darkened after 15 min to a viscous liquid, which solidified to a glass like resin on cooling. The resin gave a positive Rhodamine B test. Again hot toluene gave a suspension, from which the complete crude product was obtained on evaporation, and a third and a fourth product may be obtained as filtered solid and evaporated filtrate respectively.

EXAMPLE 3

The process of Ex.2 was repeated with 1.31 g of 2,6-dihydroxybenzoi cacid instead of 2,4-dihydroxybenzoic acid. The yield of recovered crude product was higher than in the case of Ex.2. The crude product gave a positive Rhodamine B test, commensurate with the presence of p-nonyl gamma resorcyclic calixarene. The crude product was purified by application to a silica chromatograph column and elution with hexane as a first fraction which gave a positive Rhodamine B test.

EXAMPLES 4 and 5

The products of Ex. 1 and 2 may be purified by application as solutions to a silica chromatography column and elution.

EXAMPLES 6–9

The four products of Ex. 1 and 2 are separately mixed at 6 mg/l with B99/1 II aviation base fuel, which is POSF 2827 (from USAF) and their thermal stabilizing effect tested in the Jet Fuel Thermal Oxidation Tests (JFTOT) performed as described in EPA 660077, the disclosure of which is herein incorporated by reference. Less deposit is formed by decomposition of the fuel in the presence of the products than in its absence.

EXAMPLE 10

The fuel used in Ex. 6–9 was blended with the crude and purified products of Ex.3 at 6 mg/l, and the thermal stabilising effect tested in the JFTOT test. The results were as follows, expressed volume of deposit per volume of fuel tested. Blank (fuel only), 289 ppb, fuel+crude product, 55 ppb, and Fuel+purified product 35 ppb.

We claim:

1. A method of improving the thermal stability and/or the water tolerance properties of a fuel or lubricating composition which comprises using as an additive a cyclic compound comprising m units of the formula Ia:

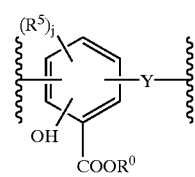

and n units of the formula (Ib):

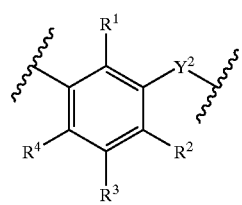

joined together to form a ring, wherein Y and $Y^2$ are divalent bridging groups which may be the same or different in each unit;

$R^0$ is H or ($C_1$–$C_6$) alkyl or is a metal or ammonium cation;

$R^5$ is H or ($C_1$–$C_{60}$) alkyl or OH group;

J is 1 or 2;

$R^3$ is hydrogen, a hydrocarbyl or a hetero-substituted hydrocarbyl group;

each of $R^1$, $R^2$ and $R^4$, which may be the same or different, is hydroxyl, hydrogen, hydrocarbyl or hetero-substituted hydrocarbyl, with the provisos that i) at least one of $R^1$, $R^2$ and $R^4$ is hydroxyl, and m+n is 4 to 20, m is 1–8 and n is at least 3, and ii) in formula Ia at least one OH group is in the meta or para position to the $COOR^0$ group and/or at least one $R^5$ group is OH.

2. A method as claimed in claim 1, wherein either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl.

3. A method as claimed in claim 1, wherein Y is $CH_2$.

4. A method as claimed in claim 2, wherein $R^1$ is hydroxyl, $R^2$ and $R^4$ are hydrogen, and $R^3$ is an alkyl of 8 to 20 carbon atoms.

5. A method as claimed in claim 1, wherein at least one of the following features (a) to (e) is met:

(a) the cyclic compound comprises at least one formula (Ia) unit in the form of a caboxylate anion, (b) the cyclic compound comprises at least one formula (Ia) unit in the form of an alkaline earth metal or alkali metal carboxylate salt, (c) the cyclic compound comprises at least 2 units of formula (Ia)

(d) the cyclic compound comprises an m+n value of 5 to 11, and (e) the cyclic compound is in the substantial absence of linear species comprising formula (Ia) and (Ib) units and/or the substantial absence of compounds of the formula (IIa) and (Ib) below;

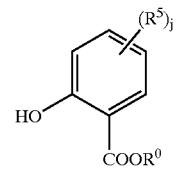

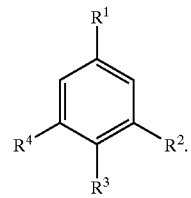

6. A method as claimed in claim 1, wherein said unit of the formula Ia has a Y group which is ortho or para to an OH group and/or is metal to the $CO_2R^0$ group.

7. A method as claimed in claim 6, wherein Y is para to an OH group and metal to a $CO_2R^0$ group.

8. A method as claimed in claim 7, wherein the unit of formula Ia is:

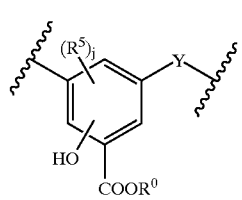

wherein one $R^5$ is OH and one $R^5$ is hydrogen.

9. A method as claimed in claim 1, wherein the unit Ia has a Y group which is ortho to said $CO_2R^0$ group.

10. A method as claimed in claim 1, wherein at least one of said units of formula Ia is derived from a mono hydroxy aromatic carboxylic acid, which is a meta or para hydroxy benzoic acid or a dihydroxycarboxylic acid.

11. A method as claimed in claim 1, wherein m is 1 or 2, and m+n is 5 to 10.

12. A method as claimed in claim 1, wherein said cyclic compound comprises seven dodecyl substituted phenolic units and one resorcinylic acid unit joined by methylene bridges.

13. A method as claimed in claim 1, wherein said cyclic compound comprises six dodecyl substituted phenolic units and two resorcinylic acid units joined by methylene bridges.

14. A method as claimed in claim 1, wherein at least one of the —$COOR^0$ groups is in the form of a potassium salt.

15. A method as claimed in claim 1, wherein said fuel composition comprises a jet fuel.

16. A method as claimed in claim 15, wherein the compound is present in a concentration of 1–1000 ppm based on the weight of the composition.

17. A method as claimed in claim 15 in which said composition comprises a linear compound having structural units of the formula Ia and Ib.

18. A method as claimed in claim 9 in which an HO group is a metal to the $CO_2R^0$ group.

19. A method as claimed in claim 10 in which the dihydroxycarboxylic acid is a 2,4,dihydroxy benzoic acid, 3,5-dihydroxy benzoic acid, 2,5-dihydroxy benzoic acid, 2,6-dihydroxy benzoic acid or 3,4,dihydroxy benzoic acid.

* * * * *